US 6,641,263 B2

(12) United States Patent
Olney

(10) Patent No.: US 6,641,263 B2
(45) Date of Patent: Nov. 4, 2003

(54) SUNGLASSES WITH REMOVABLE SEALING MEMBER

(76) Inventor: Joel William Olney, 5855 San Juan Way, Pleasanton, CA (US) 94566

( * ) Notice: Subject to any disclaimer, the term of this patent is extended or adjusted under 35 U.S.C. 154(b) by 0 days.

(21) Appl. No.: 09/929,910

(22) Filed: Aug. 14, 2001

(65) Prior Publication Data
US 2003/0035082 A1 Feb. 20, 2003

(51) Int. Cl.⁷ ............................................. G02C 11/08
(52) U.S. Cl. ........................... 351/62; 351/158; 2/436; 2/437
(58) Field of Search ........................ 351/62, 158, 41, 351/44, 47; 2/435, 436, 437

(56) References Cited

U.S. PATENT DOCUMENTS

| RE12,924 E | 3/1909 | Cover | 351/62 |
|---|---|---|---|
| 1,031,859 A | 7/1912 | Malcom | 351/62 |
| 1,433,676 A | 10/1922 | Cover | 351/62 |
| 1,478,818 A | 12/1923 | Cover | 351/62 |
| 1,562,350 A | 11/1925 | Luckey | 351/62 |
| 1,660,229 A | 5/1928 | Cook | 351/62 |
| 1,677,747 A | 7/1928 | Cook | 351/62 |
| 1,720,814 A | 7/1929 | Baker | 351/62 |
| 1,741,427 A | 12/1929 | Meyrowitz | 351/62 |
| 1,754,694 A | 4/1930 | Neuwirth | 351/62 |
| 1,846,679 A | 2/1932 | Fischer | 351/62 |
| 1,853,872 A | 4/1932 | Meyrowitz | 2/14 |
| 1,936,746 A | 11/1933 | Baker | 2/14 |
| 1,989,876 A | 2/1935 | Meyrowitz | 2/14 |
| 2,002,543 A | 5/1935 | Meyrowitz | 2/14 |
| 2,007,186 A | 7/1935 | Farrell | 2/14 |
| 2,026,435 A | 12/1935 | Ratti | 2/14 |
| 2,321,159 A | 6/1943 | Ryan | 88/41 |
| 2,364,584 A | 12/1944 | Malcom | 2/14 |
| 2,387,821 A | 10/1945 | Baratelli et al. | 2/14 |
| 2,466,048 A | 4/1949 | Kimball | 2/14 |
| 2,526,181 A | 10/1950 | Wilen | 2/14 |
| 2,608,687 A | 9/1952 | Ellis | 2/14 |
| 2,846,684 A | 8/1958 | Hill | 2/14 |
| 3,377,626 A | 4/1968 | Smith | 2/14 |

(List continued on next page.)

FOREIGN PATENT DOCUMENTS

| FR | 321010 | 7/1902 | |
|---|---|---|---|
| FR | 324973 | 10/1902 | |
| FR | 2130907 | 11/1972 | |
| GB | 127410 | 5/1918 | |
| GB | 364970 | 2/1931 | |
| JP | 56-133716 | 10/1981 | |
| JP | 4-75019 | * 3/1992 | 351/41 |

Primary Examiner—Huy Mai
(74) Attorney, Agent, or Firm—Stroock & Stroock & Lavan LLP

(57) ABSTRACT

Eyewear is disclosed for use in sports and the like which allows the wearer to attach a removable sealing member to prevent the ingress of particulate matter when active sports are engaged in which require both ventilation and sealing to keep dust, dirt and the like out of the eyes. The sealing member is removable so that when the user is engaged in more casual activities, the frame may be worn like ordinary glasses or sunglasses without the sealing member. The eyewear includes a frame shaped to fit a wearer's face, one or two lenses mounted in the frame, and a temple bracket mounted on each side of the frame. A ventilation opening can be provided on the front surface of the frame to provide an airstream which is channelled by the removable insert to provide a filtered airflow across each lens.

15 Claims, 4 Drawing Sheets

U.S. PATENT DOCUMENTS

| | | | |
|---|---|---|---|
| 3,419,909 A | 1/1969 | Spain | 2/174 |
| 3,556,644 A | 1/1971 | Stahl | 351/118 |
| 3,591,864 A | 7/1971 | Allsop | 2/14 |
| 4,264,987 A | 5/1981 | Runckel | 2/14 |
| 4,405,212 A | 9/1983 | Cooper | 351/43 |
| 4,414,693 A | 11/1983 | Brody | 2/435 |
| 4,468,819 A | 9/1984 | Ohno | 351/43 |
| 4,544,245 A | 10/1985 | Stansbury, Jr. | 351/120 |
| 4,654,899 A | 4/1987 | Harris | 2/436 |
| 4,707,863 A | 11/1987 | McNeal | 2/436 |
| D293,504 S | 1/1988 | Specht et al. | D16/107 |
| D295,533 S | 5/1988 | Wichers | D16/102 |
| 4,741,611 A | 5/1988 | Burns | 351/44 |
| 4,785,481 A | 11/1988 | Palmer, III et al. | 2/436 |
| 4,792,221 A | 12/1988 | Parks et al. | 351/120 |
| 4,877,320 A | 10/1989 | Holden | 351/44 |
| 4,955,708 A | 9/1990 | Kahaney | 351/44 |
| 5,018,223 A | 5/1991 | Dawson et al. | 2/436 |
| 5,191,364 A | 3/1993 | Kopfer | 351/62 |
| D339,596 S | 9/1993 | Kopfer | D16/102 |
| 5,428,411 A | 6/1995 | Kopfer | 351/62 |
| 5,802,622 A * | 9/1998 | Baharad et al. | 2/436 |
| D402,681 S | 12/1998 | MacWilliamson | D16/327 |
| 6,050,684 A * | 4/2000 | Mage | 351/62 |
| 6,062,688 A * | 5/2000 | Vinas | 351/47 |
| 6,067,196 A * | 6/2000 | Masumoto | 2/436 |
| D428,913 S | 8/2000 | Kopfer | D16/326 |
| 6,233,342 B1 | 5/2001 | Fernandez | 381/62 |

* cited by examiner

SUNGLASSES WITH REMOVABLE SEALING MEMBER

TECHNICAL FIELD OF THE INVENTION

This invention relates generally to eyewear for use in sports and the like; and more particularly to eyewear which is ventilated to reduce or prevent fogging, increase comfort and protect from the wind.

BACKGROUND OF THE INVENTION

Eyewear used for sports is typically designed to wrap around the user's face and sufficiently seal against the skin to create a dead air space between the glasses and the user's face (hereinafter referred to as the "dead space"). As the user engages in strenuous activity, the heat and moisture can build up in the dead space, making the glasses uncomfortable to wear and producing condensation on the inside surface of the lenses which can partially or entirely obstruct the vision of the wearer. This phenomenon is commonly known as "fogging."

There have been many prior art methods attempted to reduce or eliminate fogging. Some devices, such as that described in U.S. Pat. No. 4,707,863, describe chemical coatings which can be applied to the inside surface of a lens to alleviate fogging. Such coatings, however, tend to enhance fingerprints caused by handling, and are typically not durable, tending to wear off when the user cleans the lenses.

Therefore, different types of ventilation have been relied upon to alleviate fogging. Many prior art sunglasses and protective glasses or goggles provide openings in the frame above and below the lenses to allow air to flow in and out. These are not believed to be particularly effective at preventing fogging when a wearer is engaged in particularly strenuous activity, since there is nothing to cause the air to actually flow through the dead space, unless the wearer tilts his head downward towards the ground as he is moving forward to allow the passing air to flow through the perforations in the frame. This is not particularly desirable when the wearer is moving forward at great speed (for example, when riding a motorcycle) because such action will take the wearer's eyes off the space in front of his vehicle and may result in an unfortunate accident. Moreover, open apertures will typically allow the ingress of dust and particulate matter into the dead space where it can be blown into the unprotected eyes by the flow of air, which is also very undesirable.

U.S. Pat. Nos. 5,191,364 and 5,428,411 substantially reduced or eliminated the ingress of dust and particulate matter into the dead space by covering the ventilation apertures with permeable foam, and further addressed the fogging problem with coated and/or double lenses. However, these glasses still suffer from the lack of a motivating force for causing a flow of air through the ventilating apertures without causing the wearer to take his eyes off his direction of travel. Moreover, when the wearer is no longer engaged in active sports, and wishes to simply wear a pair of casual sunglasses to protect the eyes from the effects of sunlight while walking or driving in a closed vehicle, the foam surrounding the eyes combined with decreased airflow may cause an uncomfortable heat build up which discourages the user from wearing such eyewear for casual purposes.

British Patent Specification 364,970 addressed the problem of controlling a flow of air through the dead space by providing a valve which may be adjusted by loosening a screw, rotating an inlet regulating disc to a desired position, and then tightening the screw. This device is not desirable because the user must remove the glasses, produce a screw driver, loosen the screw, rotate the disc, tighten the screw, put the glasses back on and use them at the desired speed to determine if the disc has been rotated to a position which will produce the desired flow under the specific conditions of use. If not, the procedure must be repeated over and over again until the desired flow is obtained.

Accordingly, the need exists for sunglasses and protective glasses which automatically generate a flow of filtered air through the dead space and protects the eyes from particulate matter in the airstream when the user is engaged in active sports, and in which the seal which filters and protects the eyes can be removably detached when desired for casual wear.

SUMMARY OF THE INVENTION

In one embodiment, the present invention provides eyewear for use in both sports and casual activities having a frame shaped to fit a wearer's face, the frame including an inner surface, an outer surface, a lens mounting surface mounting a lens for protecting a wearer's eyes, a nose bridge for supporting the frame on the wearer's face, a temple bracket on each side of the frame for attaching a strap or temple bar for supporting the frame on the wearer's head, and a removable sealing member having a front surface formed to closely engage the inner surface of the frame, one or more fasteners for removably attaching the front surface of the removable sealing member to the inner surface of the frame, and a gasket covering the rear surface of the removable sealing member and ventilation openings for engaging a wearer's skin around the eyes to prevent or substantially alleviate the ingress of particulate matter.

In another embodiment, the present invention provides eyewear for use in both sports and casual activities having a frame shaped to fit a wearer's face, the frame having an inner surface, an outer surface, a pair of orbital openings for surrounding the eyes of a wearer, a nose bridge connecting said pair of orbital openings, the nose bridge including a ventilation opening containing air permeable foam for preventing the ingress of particulate matter, a lens mounting surface mounting a lens over each orbital opening, a temple bracket on each side of the frame for attaching a temple bar or strap end for supporting the frame on the wearer's head, and a removable sealing member having a pair of orbital openings connected by a nose bridge of substantially the same size and shape as the orbital openings and nose bridge of the frame, a front surface formed to closely engage the inner surface of the frame, one or more fasteners for removably attaching the front surface of the removable sealing member to the inner surface of the frame, a channel formed in the nose bridge of the removable sealing member and aligned with the ventilation opening of the frame when the sealing member is attached to said frame, the channel for diverting an airflow from the ventilation opening across an inner surface of each lens, and a gasket covering the rear surface of the removable sealing member for filtering ventilation apertures and engaging a wearer's skin around the eyes.

Other and further objects, features, advantages and embodiments of the present invention will become apparent to one skilled in the art from reading the Detailed Description of the Invention together with the drawings.

DETAILED DESCRIPTION OF THE INVENTION

Figure 1:
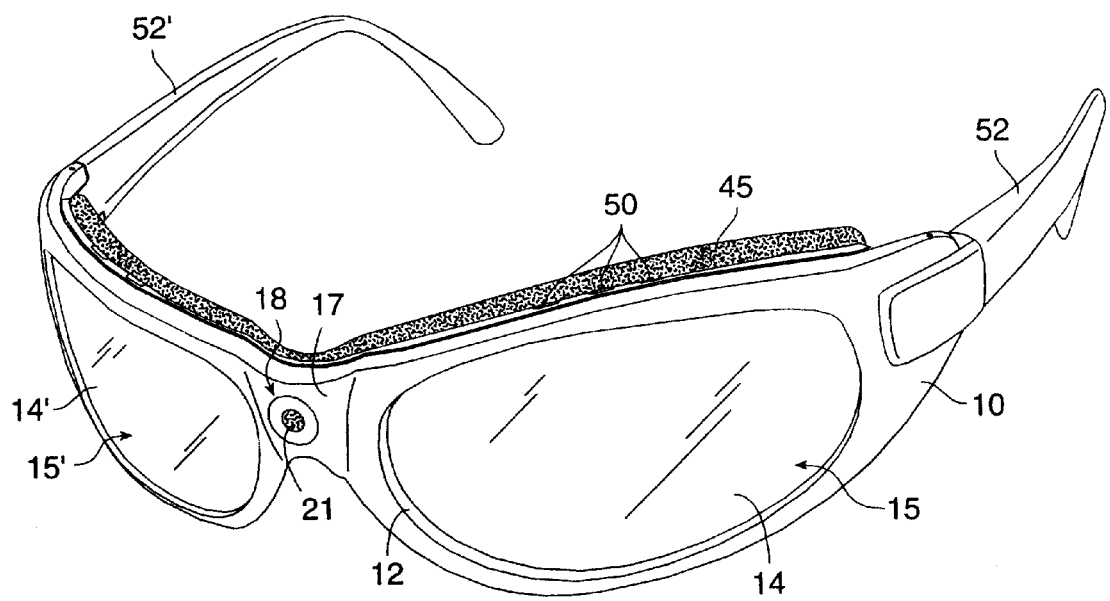
FIG. 1 is a perspective front view of eyewear of the present invention.

As shown in FIGS. 1–5, eyewear of the present invention includes a frame 10, which is preferably formed from a resilient material such as plastic. Metal frames, while less desirable, can also be used. The frame 10 includes an aperture for the eyes of the wearer which is circumscribed by a lens mounting surface 12, on which one or more lenses 14 are mounted. Lenses 14, 14' are conventionally mounted to the lens mounting surface, and may be tinted or coated to provide protection against the rays of the sun, and/or may be corrective lenses to correct the vision of far-sighted or near-sighted wearers. Most preferably, the frames 10 are provided with two eye apertures, a right eye aperture 15' aligned with the wearer's right eye and a left eye aperture 15 aligned with the wearer's left eye. However, the frame may also be constructed to provide a single aperture for both eyes, which is covered with a single lens, as shown in U.S. Pat. No. 6,233,342 which is incorporated herein by reference. Frame 10 is most preferably curved to closely fit against the wearer's face and to provide for substantially unobstructed peripheral vision.

Frames 10 are also preferably provided with a nose bridge 17 to support the eyewear on the bridge of the user's nose. Nose bridge 17 provides a convenient location on the front surface of the frame 10 which can be perforated for ventilation. In the preferred embodiment, shown in FIG. 1, a single ventilation opening 18 is provided which is covered on the outer surface 19 by a perforated vent cover 20. The opening 18 can be filled with a filtering media, such as, for example, air permeable foam 21 for filtering the air as it passes through ventilation opening 18. Other media suitable for filtering particulate matter from air may also be used. However, air permeable foam is preferred because of its light weight. A similar vent cover can be mounted on the inner surface 23 of the frame 10 for trapping the filter 21 between the two vent covers 19, 19'.

Figure 6:
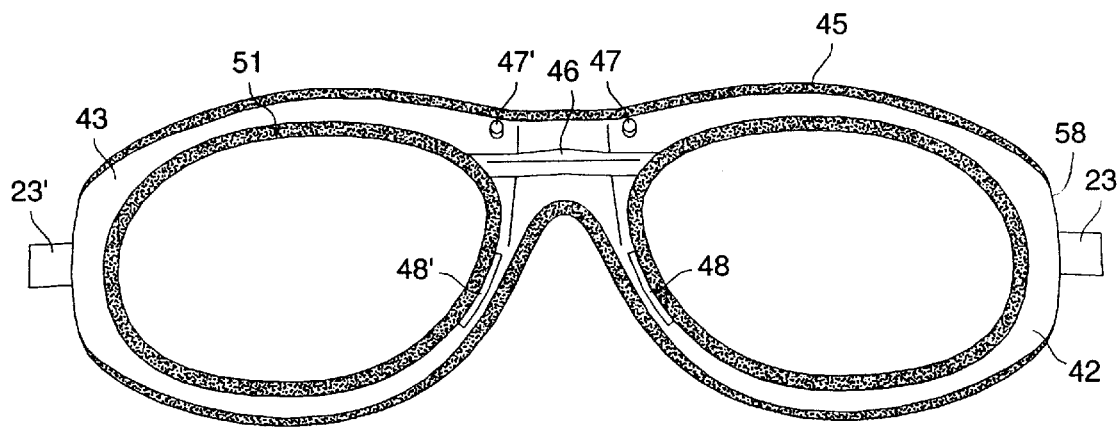
FIG. 6 is a front view of a detachable sealing member of the present invention.
Figure 7:
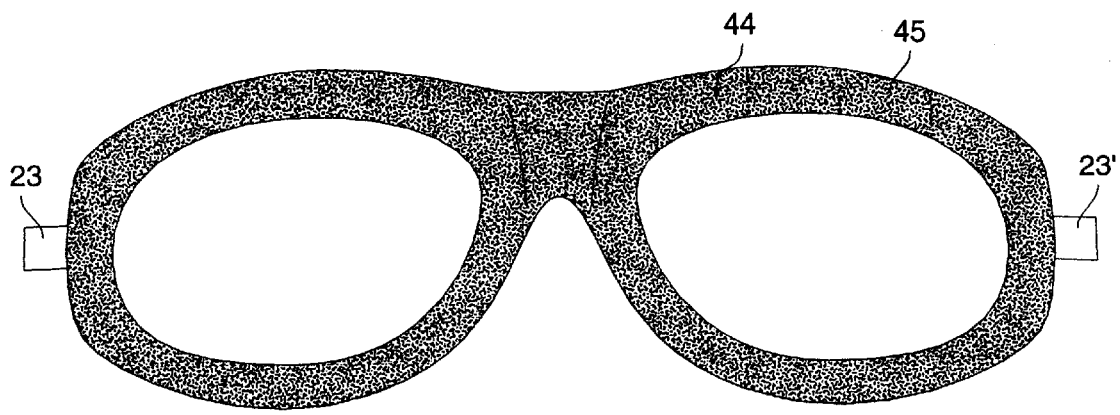
FIG. 7 is a back view of a detachable sealing member of the present invention; and, FIG. 8 is a top view of a detachable sealing member of the present invention.
Figure 8:
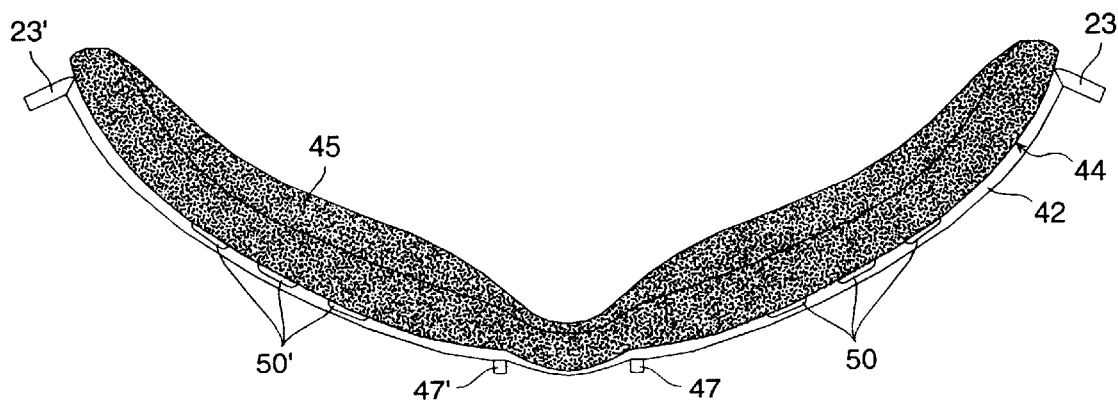

The inside of frame 10 is most preferably provided with a removable sealing member 42 contoured to fit a wearer's face closely while spacing the lenses from the wearer's face to create a dead space between the user's eyes and the lenses. Sealing member 42 is preferably covered about its periphery with a gasket 45 to provide a comfortable, cushioned seal around the wearer's face. Gasket 45 is preferably formed from air permeable foam, but may also be formed from nonpermeable foam, or textile like material. Most preferably, as shown in FIGS. 6 and 7, the gasket 45 is formed in a single, wrap-around piece to surround and cushion the user's face around the eyes, and the material preferably used is air permeable foam. As used in this application, the term "wrap around gasket" means a substantially unbroken expanse of cushioning material which wraps from the edge of the front surface 43 adjacent to the orbital opening 51 across the rear surface 44 to the outer periphery 58 of the sealing member 42, as shown in FIGS. 6 and 7.

Figure 5:
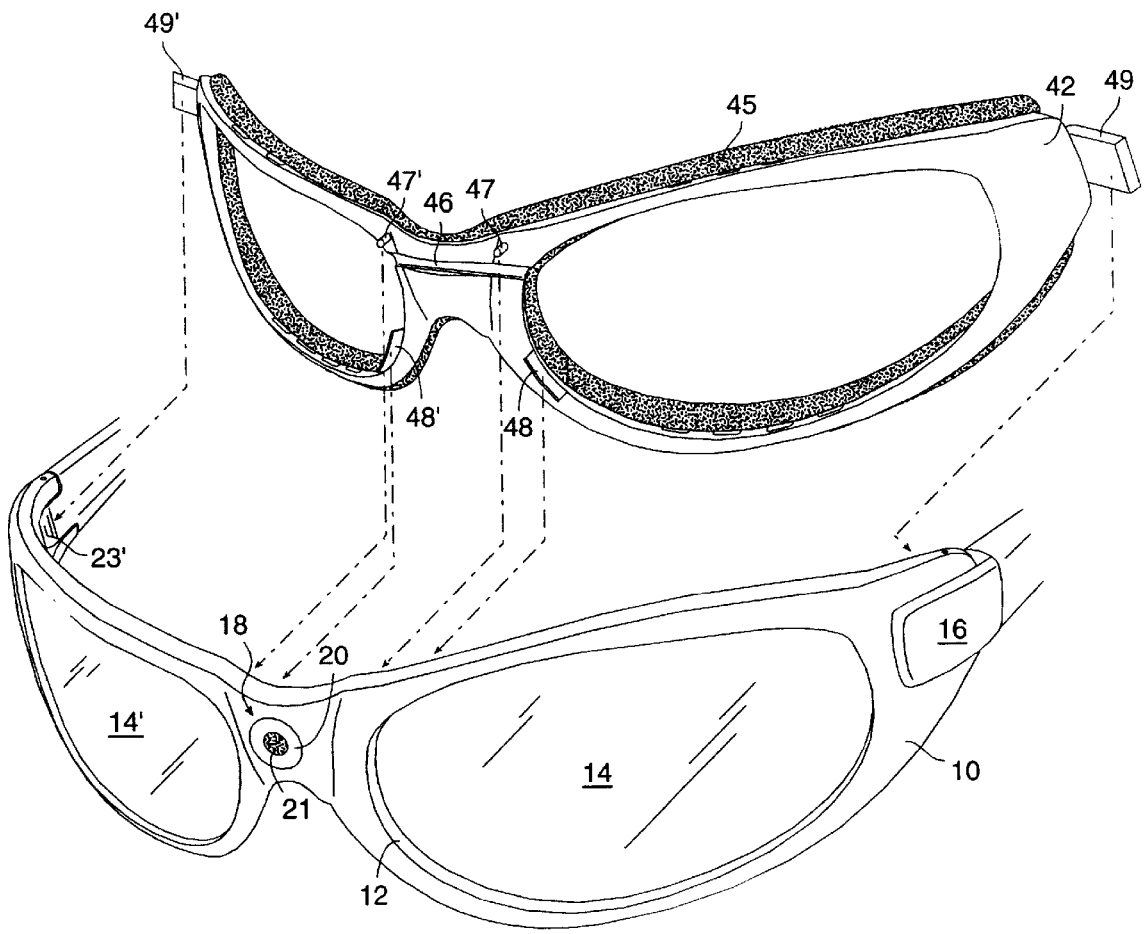
FIG. 5 is a perspective front view of the eyewear of FIG. 1 showing the detachable sealing member.

Sealing member 42 is preferably constructed from the same material as the frame 10 and most preferably is constructed from a flexible material to allow for easy insertion and removal. Sealing member 42 is provided a front surface 43 which abuts the inside of frame 10, and a rear surface 44 which is preferably covered with gasket 45 to comfortably seal against the user's face and prevent the ingress of dust and particulate matter through the space between the periphery of the glasses and the user's face. Fasteners can be used to allow for attachment and removal of the sealing member 42 to and from the frame. For example, locator pins 47, 47' and/or tabs 48, 48' are preferably provided which fit into cooperating recesses provided on the inside of frame 10. In addition, attachment tabs 49, 49' are preferably provided at each end of sealing member 42 for securing the front surface 43 of the sealing member 42 against the inside of frame 10. As shown in FIG. 5, to attach the sealing member, an attachment tab 49' can be slid into slot 23', preferably located on the right side of frame 10, locator pins 47, 47' and tabs 48, 48' pushed into their receiving recesses on the inside of frame 10, and the sealing member 42 is flexed to slide attachment tab 49 into position in slot 23, preferably located on the left side of frame 10. The curvature of the sealing member 42, and angle of attachment tab 49, 49' and receiving slots 23, 23' hold the sealing member 42 securely against the inside surface of frame 10. To remove sealing member 42, the user need only grasp the sealing member 42 adjacent to one of the attachment tabs 49, 49' and pull to disengage one end, whereupon the entire sealing member 42 can be easily removed. While less preferred, any other conventional fasteners useful for removable attachment can also be used, such as, for example, studs for engaging keyed slots, conventional threaded fasteners, sliding fasteners, rotating fasteners, latches, and the like.

A channel 46 is preferably provided on the front surface 43 of the sealing member when the sealing member 42 is used with the preferred embodiment shown in FIG. 1 having a ventilation opening 18 for diverting the flow of air traveling through the ventilation opening 18 and foam 22 across the inside surfaces of lenses 14, 14'. When so provided, channel 46 should be aligned with the ventilation opening 18 when sealing member 42 is attached to frame 10. Ventilation openings 50, 50' may also be provided in the top and/or bottom of the sealing member 42 whereby the air stream moving through the ventilation opening 18 is diverted by channel 46 across the inner surface of lenses 14, 14' to alleviate fogging, and out of the dead space through ventilation openings 50, 50' which extend from the edge of the orbital openings 51 to a peripheral edge of the sealing member 42. Most preferably, ventilation openings 50, 50' are covered on the inside by gasket 45.

Figure 2:
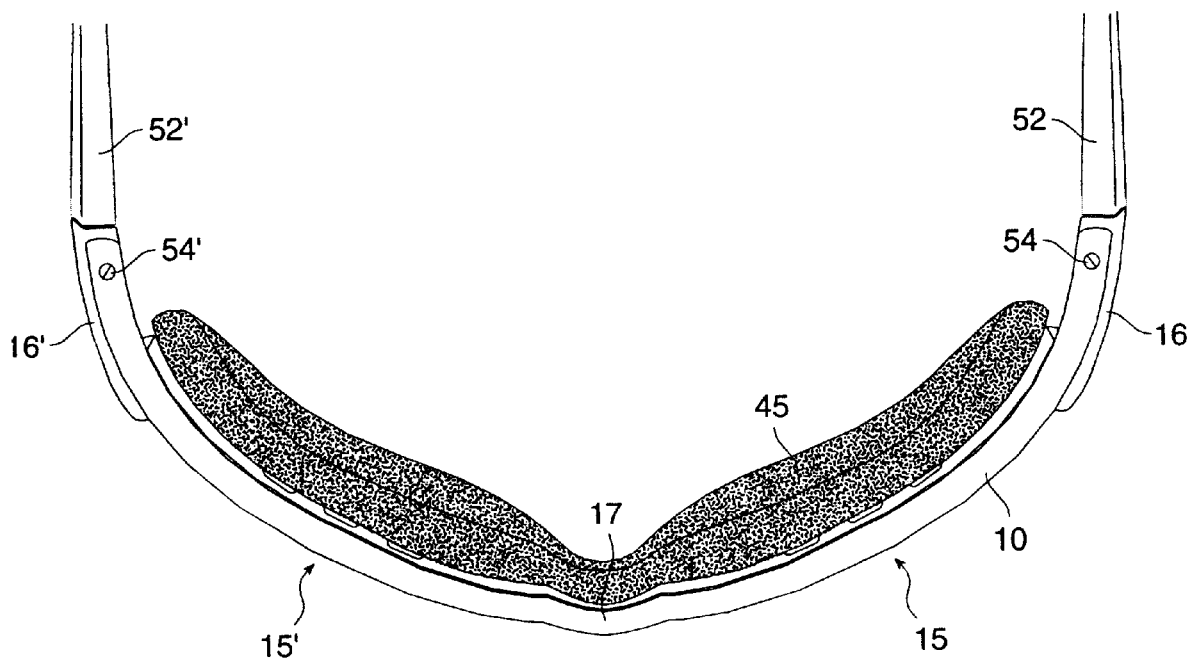
FIG. 2 is a perspective top view of the eyewear of FIG. 1.
Figure 3:
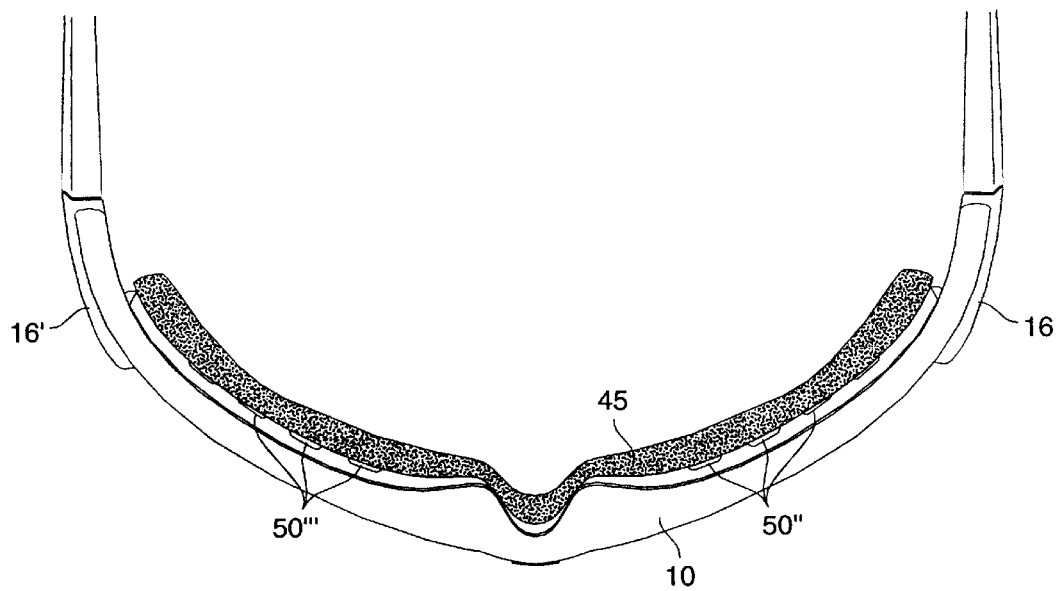
FIG. 3 is a bottom view of the eyewear of FIG. 1.
Figure 4:
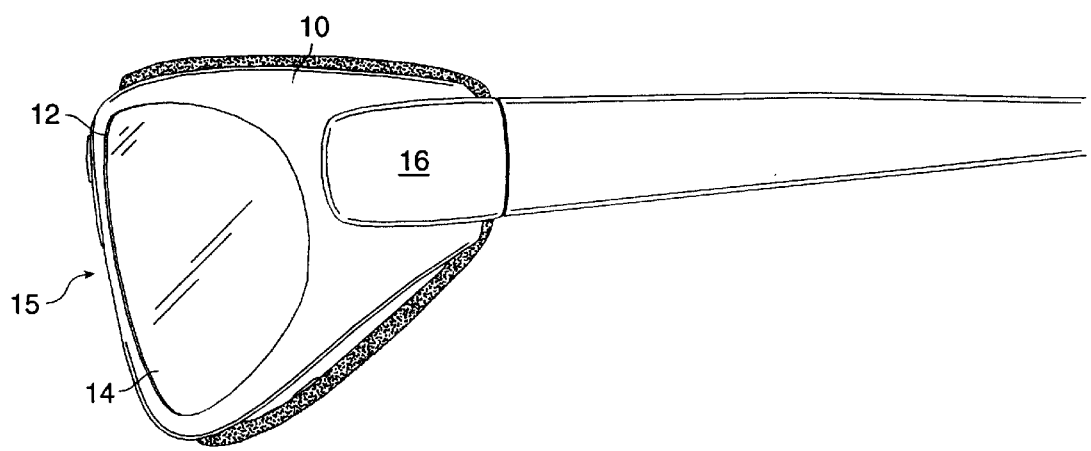
FIG. 4 is a side view of the eyewear of FIG. 1.

A pair of temple bars 52, 52', shown in FIGS. 1 and 2, or an adjustable elastic strap (shown in U.S. Pat. No. 6,233,342 incorporated herein by reference), can be conventionally used to support the frames 10 on the user's head. The rear surface of temple bracket 16, 16' respectively, provides a convenient surface for connecting the temple bars 52, 52' or strap to the frame. Temple bracket 16, 16' need not be a separate structure, but may simply be the end portion of the frame to which the temple bars 52, 52' or strap can be attached. Temple bars 52, 52' are preferably connected conventionally to the frame to allow the bars 52, 52' to pivot around a hinge pin 54, 54' for selectively folding the bars 52, 52' to a closed position towards the inner surface of the frame or to an open position for mounting on the wearer's head in the well-known conventional fashion. Temple bars 52, 52' may be permanently mounted for such pivoting movement, or may be removably mounted using well-known, bayonet type mounts which allow for removal of the temple bars 52, 52' and replacement by a strap. Likewise, a strap may be permanently or removably mounted to the rear surface of temple bracket 16, 16'. The length of the strap can be conventionally adjusted using a buckle or other adjustment means to provide a snug fit against the wearer's face.

In use the present invention is particularly advantageous to users who wish to use the same pair of sportsglasses for vigorous activities, such as skiing, which involve speed, and thus require both ventilation and protection against airborne particulate matter, and for casual activities where protection against airborne particulate matter is not critical and where it may not be desirable to wear sportsglasses having a seal around the user's face. For vigorous activities involving speed, the user simply inserts the sealing member 42 to the frame as described above. As the user moves, air is directed through ventilation opening 18, where any particulate matter is trapped by the filter 22. As the air passes through ventilation opening 18, it encounters channel 46 which splits the airstream in two, directing it to the right and the left across the inner surface of each lens. This airflow alleviates any tendency to fog and constantly changes the air in the dead space to prevent a buildup of heat or humidity as the user exercises. The airflow can then exit through ventilation openings 50, 50' When the user has finished the sporting activity, and returns to a more casual environment, she can remove the sealing member as described above and wear the frame as one would wear ordinary sunglasses. Air can still flow through the ventilation opening 18, but filter 22 prevents particulate matter from being blown directly into the eyes.

One skilled in the art will recognize at once that it would be possible to construct the present invention from a variety of materials and in a variety of different ways. While the preferred embodiments have been described in detail, and shown in the accompanying drawings, it will be evident that various further modification are possible without departing from the scope of the invention as set forth in the appended claims.

What is claimed is:

1. Eyewear for use both in sports and casual activities, comprising:
   a frame shaped to fit a wearer's face having an inner surface, an outer surface, a lens mounting surface for mounting a lens means for Protecting a wearer's eyes, at least one lens mounted on said lens mounting surface, a nose bridge for supporting said frame on said wearer's face including a ventilation opening through said nose bridge, a temple bracket on each side of the frame for attaching a means for supporting the frame on the wearer's head and; and
   a removable sealing member having a front surface formed to closely engage the inner surface of said frame, a rear surface, one of more fasteners for removably attaching the front surface of the removable sealing member to the inner surface of the frame, and a gasket covering one or more ventilation openings and the rear surface of the removable sealing member for engaging a wearer's skin around the eyes.

2. The eyewear of claim 1 wherein said ventilation opening is filled with air permeable foam to prevent the ingress of particulate matter.

3. The eyewear of claim 2 wherein said removable sealing member includes a sealing member nose bridge for engaging said nose bridge of said frame, and wherein said sealing member nose bridge is provided with a channel aligned with said ventilation opening when said sealing member is attached to said frame for directing a flow of air passing through said ventilation opening across each said lens.

4. Eyewear for use both in sports and casual activities, comprising:
   a frame shaped to fit a wearer's face having an inner surface, an outer surface, a lens mounting surface for mounting a lens means for protecting a wearer's eyes, at least one lens mounted on said lens mounting surface, a nose bridge for supporting said frame on said wearer's face, a temple bracket on each side of the frame for attaching a means for supporting the frame on the wearer's head; and
   a removable sealing member having a front surface formed to closely engage the inner surface of said frame, a rear surface, one of more fasteners for removably attaching the front surface of the removable sealing member to the inner surface of the frame comprising a first attachment tab at one end of said sealing member for engaging a first recess provided behind one of said temple brackets, a second attachment tab at an opposite end of said sealing member for engaging a second recess provided behind the other of said temple brackets, and a locator means positioned between said first attachment tab and said second attachment tab for engaging a cooperating structure provided on said inner surface of said frame, and a gasket covering one or more ventilation openings and the rear surface of the removable sealing member for engaging a wearer's skin around the eyes.

5. The eyewear of claim 4 wherein said locator means includes a first locator pin positioned to engage a first locator recess on said inner surface of said frame to one side of said nose bridge and a second locator pin positioned to engage a second locator recess on said inner surface of said frame to an opposite side of said nose bridge from said first locator recess.

6. The eyewear of claim 5 further comprising a first locator tab positioned below said first locator pin for engaging a first tab recess on said inner surface of said frame, and a second locator tab positioned below said second locator pin for engaging a second tab recess on said inner surface of said frame.

7. Eyewear for use both in sports and in casual activities, comprising:
   a frame shaped to fit a wearer's face, said frame having an inner surface, an outer surface, a pair of orbital openings for surrounding the eyes of a wearer, a nose bridge connecting said pair of orbital openings, said nose bridge including a ventilation opening containing air permeable foam for preventing the ingress of particulate matter, a lens mounting surface mounting a lens over each orbital opening, a temple bracket on each side of the frame for attaching a means for supporting the frame on the wearer's head; and,
   a removable sealing member having a pair of orbital openings connected by a nose bridge of substantially the same size and shape as said orbital openings and nose bridge of said frame, a front surface formed to closely engage the inner surface of said frame, a rear surface, attachment means for removably attaching the front surface of the removable sealing member to the inner surface of the frame, a channel formed in said nose bridge of said sealing member in a position to be aligned with said ventilation opening of said frame when said sealing member is attached to said frame for diverting an airflow from said ventilation opening across an inner surface of each said lens, and a gasket covering the rear surface of the removable sealing member for engaging a wearer's skin around the eyes.

8. The eyewear of claim 7 wherein said gasket is formed from air permeable foam.

9. The eyewear of claim 8 wherein said gasket is a wraparound foam gasket.

10. The eyewear of claim 8 wherein said removable sealing member includes one or more ventilation openings extending from each said orbital opening to a peripheral edge, said ventilation openings covered by said foam gasket to prevent the ingress of particulate matters.

11. The eyewear of claim 8 wherein said means for supporting the frame to the head of the wearer comprises an elastic strap having a first and a second end, said first end mounted to said rear surface of one of said temple brackets, and said second end mounted to said rear surface of the other of said temple brackets.

12. The eyewear of claim 7 wherein said means for supporting the frame to the head of the wearer comprises a temple bar hingedly mounted to the rear surface of each temple bracket, said temple bar shaped to fit a user's head in a region above and behind a user's ears.

13. Eyewear for use in sports and casual activities, comprising:
   a frame having an inner surface, an outer surface and at least one lens mounted therein wherein said frame comprises a nose bridge for supporting the frame on a wearer's face, and wherein said nose bridge comprises a ventilation opening therein; and
   a removable sealing member having a front surface formed to closely engage the inner surface of said frame, a rear surface, and one or more fasteners for removably attaching the removable sealing member to the frame, wherein said sealing member comprises a gasket on at least a portion of said rear surface for engaging a wearer's skin.

14. The eyewear of claim 13, wherein said ventilation opening is filled with air permeable foam.

15. The eyewear of claim 14, wherein said ventilation opening in said nose bridge extends through the outer surface of said frame.

* * * * *